US010149812B2

(12) United States Patent
Stocklin et al.

(10) Patent No.: US 10,149,812 B2
(45) Date of Patent: *Dec. 11, 2018

(54) COSMETIC COMPOSITION COMPRISING A MUCONOPEPTIDE

(71) Applicant: ACTIVEN, Lausanne (CH)

(72) Inventors: Reto Stocklin, Avusy (CH); Jean-Marc Le Doussal, Lausanne (CH); Louis Lamy, Orlienas (FR); Bethsabee Coutaz, Neuilly sur Seine (FR)

(73) Assignee: ACTIVEN, Lausanne (CH)

( * ) Notice: Subject to any disclaimer, the term of this patent is extended or adjusted under 35 U.S.C. 154(b) by 6 days.

This patent is subject to a terminal disclaimer.

(21) Appl. No.: 15/391,113

(22) Filed: Dec. 27, 2016

(65) Prior Publication Data

US 2017/0157016 A1 Jun. 8, 2017

Related U.S. Application Data

(63) Continuation-in-part of application No. 14/391,455, filed as application No. PCT/EP2013/057850 on Apr. 15, 2013, now Pat. No. 9,566,227.

(60) Provisional application No. 61/623,913, filed on Apr. 13, 2012.

(30) Foreign Application Priority Data

Apr. 17, 2012 (WO) ................. PCT/EP2012/057026

(51) Int. Cl.
*A61K 8/64* (2006.01)
*A61Q 19/08* (2006.01)
*A61K 38/17* (2006.01)

(52) U.S. Cl.
CPC ............ *A61K 8/64* (2013.01); *A61K 38/1767* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 2003/0050234 A1 | 3/2003 | Olivera et al. |
| 2004/0204362 A1 | 10/2004 | Olivera et al. |
| 2008/0005031 A1 | 1/2008 | Kamio et al. |
| 2008/0050318 A1 | 2/2008 | Renault |
| 2010/0021510 A1 | 1/2010 | Carreno Serraima et al. |

FOREIGN PATENT DOCUMENTS

| | | |
|---|---|---|
| EP | 1180524 | 2/2002 |
| EP | 2123673 | 11/2009 |
| WO | 02/07678 | 1/2002 |
| WO | 2004/099238 | 11/2004 |
| WO | 2006/047900 | 5/2006 |
| WO | 2007/054785 | 5/2007 |
| WO | 2007/071448 | 6/2007 |
| WO | 2009/012376 | 1/2009 |
| WO | 2011/048443 | 4/2011 |

OTHER PUBLICATIONS

International Search Report dated Jan. 8, 2014, corresponding to PCT/EP2013/057850.
Iti, et al.; "Status of Surfactants as Penetration Enhancers in Transdermal Drug Delibvery"; vol. 4, No. 1; Feb. 9, 2012, pp. 1-11.
Gayathri Krishnan, et al.; "Enhanced Transdermal Delivery of 5-Aminolevulinic Acid and a Dipeptide by Iontophoresis"; vol. 96, No. 2, 2011; pp. 166-171.
Philippe Favreau, et al.; "Marine Snail Venoms: Use and Trends in Receptor and Channel Neuropharmacology"; vol. 9, No. 5; Oct. 2009; pp. 594-601.
Philippe Favreau, et al.; "A Novel—Conopeptide, CnIIIC, Exerts Potent and Preferential Inhibition NaV1.2/1.4 Channels and Blocks Neuronal Nicotinic Acetylcholine Receptors"; vol. 166, No. 5; Jul. 2012; pp. 1654-1668.
http://www.aocd.org/?page=Hyperpigmentation , accessed Oct. 20, 2015.
Carmago et al. "Botulism toxin for facial wrinkles" The Cochrane Library 2014, Issue 9.
O.P. Hamill, et al.; "Improved Patch-Clamp Techniques for High-Resolution Current Recording from Cells and Cell-Free Membrane Patches"; European Journal of Physiology; May 27, 1981; pp. 85-100.
P.Velez, et al.; "A functional assay for paralytic shellfish toxins that uses recombinant sodium channels"; Toxicon; 2001; pp. 929-935.
T. Yamagishi, et al.; "Topology of the P Segments in the Sodium Channel Pore Revealed by Cysteine Mutagenesis"; Biophysical Journal; vol. 73; Jul. 1997; pp. 195-204.

*Primary Examiner* — James H Alstrum-Acevedo
*Assistant Examiner* — Tara L Martinez
(74) *Attorney, Agent, or Firm* — Young & Thompson

(57) ABSTRACT

A cosmetic composition containing as an active substance a cosmetically effective amount of at least one mu-conotoxin peptide is provided. In particular, a composition wherein the mu-conotoxin peptide is Arginine, lysine polypeptide (INCI name: pyroglutamyl s-mu-conotoxin CnIIIc amide acetate), CAS Number: 937286-43-6 (renumbered 936616-33-0), Molecular formula $C_{92}$,$H_{139}$,$N_{35}$,$O_{28}$,$S_6$ acetate salt (molar mass 2376 g/mol.) is provided. The composition can be used to improve the mechanical properties of the skin, tonicity and/or firmness and/or elasticity of the skin.

11 Claims, 4 Drawing Sheets

Specification includes a Sequence Listing.

SEQUENCE LISTING

```
<160> NUMBER OF SEQ ID NOS: 21

<210> SEQ ID NO 1
<211> LENGTH: 23
<212> TYPE: PRT
<213> ORGANISM: Conus sp.
<220> FEATURE:
<221> NAME/KEY: MISC_FEATURE
<222> LOCATION: (1)..(1)
<223> OTHER INFORMATION: X is any N-modified amino acid
<220> FEATURE:
<221> NAME/KEY: MISC_FEATURE
<222> LOCATION: (5)..(5)
<223> OTHER INFORMATION: X is any acidic amino acid or any of its amide
      form
<220> FEATURE:
<221> NAME/KEY: MISC_FEATURE
<222> LOCATION: (7)..(7)
<223> OTHER INFORMATION: X is proline or 3-hydroxyl proline
<220> FEATURE:
<221> NAME/KEY: MISC_FEATURE
<222> LOCATION: (8)..(8)
```

```
<223> OTHER INFORMATION: X is any basic amino acid
<220> FEATURE:
<221> NAME/KEY: MISC_FEATURE
<222> LOCATION: (11)..(11)
<223> OTHER INFORMATION: X is any non-aromatic hydroxyl amino acid
<220> FEATURE:
<221> NAME/KEY: MISC_FEATURE
<222> LOCATION: (12)..(12)
<223> OTHER INFORMATION: X is any non-aromatic hydroxyl amino acid
<220> FEATURE:
<221> NAME/KEY: MISC_FEATURE
<222> LOCATION: (13)..(13)
<223> OTHER INFORMATION: X is any basic amino acid
<220> FEATURE:
<221> NAME/KEY: MISC_FEATURE
<222> LOCATION: (14)..(14)
<223> OTHER INFORMATION: X is any aromatic amino acid
<220> FEATURE:
<221> NAME/KEY: MISC_FEATURE
<222> LOCATION: (16)..(16)
<223> OTHER INFORMATION: X is any basic amino acid
<220> FEATURE:
<221> NAME/KEY: MISC_FEATURE
<222> LOCATION: (17)..(17)
<223> OTHER INFORMATION: X is any acidic amino acid or any of its amide
      form
<220> FEATURE:
<221> NAME/KEY: MISC_FEATURE
<222> LOCATION: (18)..(18)
<223> OTHER INFORMATION: X is any basic amino acid, or any sulfur-
      containing amino acid
<220> FEATURE:
<221> NAME/KEY: MISC_FEATURE
<222> LOCATION: (19)..(19)
<223> OTHER INFORMATION: X is any hydrophobic or apolar amino acid, or
      any non-aromatic hydroxyl amino acid
<220> FEATURE:
<221> NAME/KEY: MISC_FEATURE
<222> LOCATION: (20)..(20)
<223> OTHER INFORMATION: X is any basic amino acid
<220> FEATURE:
<221> NAME/KEY: MISC_FEATURE
<222> LOCATION: (23)..(23)
<223> OTHER INFORMATION: X is any apolar amino acid, or an amide group

<400> SEQUENCE: 1

Xaa Gly Cys Cys Xaa Gly Pro Xaa Gly Cys Xaa Xaa Xaa Xaa Cys Xaa
1               5                   10                  15

Xaa Xaa Xaa Xaa Cys Cys Xaa
            20


<210> SEQ ID NO 2
<211> LENGTH: 23
<212> TYPE: PRT
<213> ORGANISM: Conus sp.
<220> FEATURE:
<221> NAME/KEY: MISC_FEATURE
<222> LOCATION: (1)..(1)
<223> OTHER INFORMATION: X is pyroglutamate
<220> FEATURE:
<221> NAME/KEY: MISC_FEATURE
<222> LOCATION: (23)..(23)
<223> OTHER INFORMATION: X is amide

<400> SEQUENCE: 2

Glx Gly Cys Cys Asn Gly Pro Lys Gly Cys Ser Ser Lys Trp Cys Arg
1               5                   10                  15

Asp His Ala Arg Cys Cys Xaa
            20


<210> SEQ ID NO 3
<211> LENGTH: 22
<212> TYPE: PRT
```

```
<213> ORGANISM: Conus sp.
<220> FEATURE:
<221> NAME/KEY: MISC_FEATURE
<222> LOCATION: (1)..(1)
<223> OTHER INFORMATION: X is any N-modified amino acid
<220> FEATURE:
<221> NAME/KEY: MISC_FEATURE
<222> LOCATION: (5)..(5)
<223> OTHER INFORMATION: X is any acidic amino acid or any of its amide
      form
<220> FEATURE:
<221> NAME/KEY: MISC_FEATURE
<222> LOCATION: (7)..(7)
<223> OTHER INFORMATION: X is proline or 3-hydroxyl proline
<220> FEATURE:
<221> NAME/KEY: MISC_FEATURE
<222> LOCATION: (8)..(8)
<223> OTHER INFORMATION: X is any basic amino acid
<220> FEATURE:
<221> NAME/KEY: MISC_FEATURE
<222> LOCATION: (11)..(11)
<223> OTHER INFORMATION: X is any non-aromatic hydroxyl amino acid
<220> FEATURE:
<221> NAME/KEY: MISC_FEATURE
<222> LOCATION: (12)..(12)
<223> OTHER INFORMATION: X is any non-aromatic hydroxyl amino acid
<220> FEATURE:
<221> NAME/KEY: MISC_FEATURE
<222> LOCATION: (13)..(13)
<223> OTHER INFORMATION: X is any basic amino acid
<220> FEATURE:
<221> NAME/KEY: MISC_FEATURE
<222> LOCATION: (14)..(14)
<223> OTHER INFORMATION: X is any aromatic amino acid
<220> FEATURE:
<221> NAME/KEY: MISC_FEATURE
<222> LOCATION: (16)..(16)
<223> OTHER INFORMATION: X is any basic amino acid
<220> FEATURE:
<221> NAME/KEY: MISC_FEATURE
<222> LOCATION: (17)..(17)
<223> OTHER INFORMATION: X is any acidic amino acid or any of its amide
      form
<220> FEATURE:
<221> NAME/KEY: MISC_FEATURE
<222> LOCATION: (18)..(18)
<223> OTHER INFORMATION: X is any basic amino acid, or any sulfur-
      containing amino acid
<220> FEATURE:
<221> NAME/KEY: MISC_FEATURE
<222> LOCATION: (19)..(19)
<223> OTHER INFORMATION: X is any hydrophobic or apolar amino acid, or
      any non-aromatic hydroxyl amino acid
<220> FEATURE:
<221> NAME/KEY: MISC_FEATURE
<222> LOCATION: (20)..(20)
<223> OTHER INFORMATION: X is any basic amino acid

<400> SEQUENCE: 3

Xaa Gly Cys Cys Xaa Gly Pro Xaa Gly Cys Xaa Xaa Xaa Xaa Cys Xaa
1               5                   10                  15

Xaa Xaa Xaa Xaa Cys Cys
            20


<210> SEQ ID NO 4
<211> LENGTH: 23
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
```

<222> LOCATION: (23)..(23)
<223> OTHER INFORMATION: X is amide

<400> SEQUENCE: 4

Xaa Gly Cys Cys Asn Gly Pro Arg Gly Cys Ser Ser Lys Trp Cys Arg
1               5                   10                  15

Asp His Ala Arg Cys Cys Xaa
            20

<210> SEQ ID NO 5
<211> LENGTH: 23
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (23)..(23)
<223> OTHER INFORMATION: X is amide

<400> SEQUENCE: 5

Xaa Gly Cys Cys Asn Gly Pro Lys Gly Cys Ser Ser Arg Trp Cys Arg
1               5                   10                  15

Asp His Ala Arg Cys Cys Xaa
            20

<210> SEQ ID NO 6
<211> LENGTH: 23
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (23)..(23)
<223> OTHER INFORMATION: X is amide

<400> SEQUENCE: 6

Xaa Gly Cys Cys Asn Gly Pro Lys Gly Cys Ser Ser Lys Trp Cys Arg
1               5                   10                  15

Asp Arg Ala Arg Cys Cys Xaa
            20

<210> SEQ ID NO 7
<211> LENGTH: 23
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (23)..(23)
<223> OTHER INFORMATION: X is amide

<400> SEQUENCE: 7

Xaa Gly Cys Cys Asn Gly Pro Lys Gly Cys Ser Ser Lys Phe Cys Arg
1               5                   10                  15

Asp His Ala Arg Cys Cys Xaa
20

<210> SEQ ID NO 8
<211> LENGTH: 24
<212> TYPE: PRT
<213> ORGANISM: Artificial Sequence
<220> FEATURE:
<223> OTHER INFORMATION: CnIIIC variant
<220> FEATURE:
<221> NAME/KEY: LIPID
<222> LOCATION: (1)..(1)
<223> OTHER INFORMATION: PALMITATE
<220> FEATURE:
<221> NAME/KEY: MISC_FEATURE
<222> LOCATION: (24)..(24)
<223> OTHER INFORMATION: X is amide

<400> SEQUENCE: 8

Xaa Lys Gly Cys Cys Asn Gly Pro Lys Gly Cys Ser Ser Lys Trp Cys
1 5 10 15

Arg Asp His Ala Arg Cys Cys Xaa
20

<210> SEQ ID NO 9
<211> LENGTH: 24
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: Oleyl
<220> FEATURE:
<221> NAME/KEY: MISC_FEATURE
<222> LOCATION: (24)..(24)
<223> OTHER INFORMATION: X is amide

<400> SEQUENCE: 9

Xaa Lys Gly Cys Cys Asn Gly Pro Lys Gly Cys Ser Ser Lys Trp Cys
1 5 10 15

Arg Asp His Ala Arg Cys Cys Xaa
20

<210> SEQ ID NO 10
<211> LENGTH: 24
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: Stearyl
<220> FEATURE:
<221> NAME/KEY: MISC_FEATURE
<222> LOCATION: (24)..(24)
<223> OTHER INFORMATION: X is amide

<400> SEQUENCE: 10

Xaa Lys Gly Cys Cys Asn Gly Pro Lys Gly Cys Ser Ser Lys Trp Cys
1 5 10 15

Arg Asp His Ala Arg Cys Cys Xaa
20

<210> SEQ ID NO 11
<211> LENGTH: 24

<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: Decanoyl
<220> FEATURE:
<221> NAME/KEY: MISC_FEATURE
<222> LOCATION: (24)..(24)
<223> OTHER INFORMATION: X is amide

<400> SEQUENCE: 11

```
Xaa Lys Gly Cys Cys Asn Gly Pro Lys Gly Cys Ser Ser Lys Trp Cys
1               5                   10                  15

Arg Asp His Ala Arg Cys Cys Xaa
            20
```

<210> SEQ ID NO 12
<211> LENGTH: 24
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: Lauryl
<220> FEATURE:
<221> NAME/KEY: MISC_FEATURE
<222> LOCATION: (24)..(24)
<223> OTHER INFORMATION: X is amide

<400> SEQUENCE: 12

```
Xaa Lys Gly Cys Cys Asn Gly Pro Lys Gly Cys Ser Ser Lys Trp Cys
1               5                   10                  15

Arg Asp His Ala Arg Cys Cys Xaa
            20
```

<210> SEQ ID NO 13
<211> LENGTH: 24
<212> TYPE: PRT
<213> ORGANISM: Artificial Sequence
<220> FEATURE:
<223> OTHER INFORMATION: CnIIIC variant
<220> FEATURE:
<221> NAME/KEY: LIPID
<222> LOCATION: (1)..(1)
<223> OTHER INFORMATION: MYRISTATE
<220> FEATURE:
<221> NAME/KEY: MISC_FEATURE
<222> LOCATION: (24)..(24)
<223> OTHER INFORMATION: X is amide

<400> SEQUENCE: 13

```
Xaa Lys Gly Cys Cys Asn Gly Pro Lys Gly Cys Ser Ser Lys Trp Cys
1               5                   10                  15

Arg Asp His Ala Arg Cys Cys Xaa
            20
```

<210> SEQ ID NO 14
<211> LENGTH: 23
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)

-continued

<223> OTHER INFORMATION: X is pyroglutamate (pGlu)
<220> FEATURE:
<221> NAME/KEY: MISC_FEATURE
<222> LOCATION: (23)..(23)
<223> OTHER INFORMATION: X is amide

<400> SEQUENCE: 14

```
Xaa Gly Cys Cys Asn Gly Pro Lys Gly Cys Ser Ser Lys Tyr Cys Arg
1               5                   10                  15

Asp His Ala Arg Cys Cys Xaa
            20
```

<210> SEQ ID NO 15
<211> LENGTH: 23
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (23)..(23)
<223> OTHER INFORMATION: X is amide

<400> SEQUENCE: 15

```
Xaa Gly Cys Cys Asp Gly Pro Lys Gly Cys Ser Ser Lys Trp Cys Arg
1               5                   10                  15

Asp His Ala Arg Cys Cys Xaa
            20
```

<210> SEQ ID NO 16
<211> LENGTH: 23
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (23)..(23)
<223> OTHER INFORMATION: X is amide

<400> SEQUENCE: 16

```
Xaa Gly Cys Cys Asn Gly Pro Lys Gly Cys Thr Ser Lys Trp Cys Arg
1               5                   10                  15

Asp His Ala Arg Cys Cys Xaa
            20
```

<210> SEQ ID NO 17
<211> LENGTH: 23
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (23)..(23)
<223> OTHER INFORMATION: X is amide

<400> SEQUENCE: 17

Xaa Gly Cys Cys Glu Gly Pro Lys Gly Cys Ser Ser Lys Trp Cys Arg
1 5 10 15

Asp His Ala Arg Cys Cys Xaa
20

<210> SEQ ID NO 18
<211> LENGTH: 23
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (23)..(23)
<223> OTHER INFORMATION: X is amide

<400> SEQUENCE: 18

Xaa Gly Cys Cys Gln Gly Pro Lys Gly Cys Ser Ser Lys Trp Cys Arg
1 5 10 15

Asp His Ala Arg Cys Cys Xaa
20

<210> SEQ ID NO 19
<211> LENGTH: 23
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (23)..(23)
<223> OTHER INFORMATION: X is amide

<400> SEQUENCE: 19

Xaa Gly Cys Cys Asn Gly Pro Lys Gly Cys Ser Ser Lys Trp Cys Arg
1 5 10 15

Asp His Ser Arg Cys Cys Xaa
20

<210> SEQ ID NO 20
<211> LENGTH: 21
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (21)..(21)
<223> OTHER INFORMATION: X is amide

<400> SEQUENCE: 20

Xaa Gly Cys Cys Pro Lys Gly Cys Ser Ser Lys Trp Cys Arg Asp His
1 5 10 15

Ala Arg Cys Cys Xaa
20

-continued

```
<210> SEQ ID NO 21
<211> LENGTH: 21
<212> TYPE: PRT
<213> ORGANISM: Artificial Sequence
<220> FEATURE:
<223> OTHER INFORMATION: CnIIIC variant
<220> FEATURE:
<221> NAME/KEY: MISC_FEATURE
<222> LOCATION: (1)..(1)
<223> OTHER INFORMATION: X is pyroglutamate (pGlu)
<220> FEATURE:
<221> NAME/KEY: MISC_FEATURE
<222> LOCATION: (21)..(21)
<223> OTHER INFORMATION: X is amide

<400> SEQUENCE: 21

Xaa Gly Cys Cys Asn Gly Pro Lys Gly Cys Lys Trp Cys Arg Asp His
1               5                   10                  15

Ala Arg Cys Cys Xaa
            20
```

COSMETIC COMPOSITION COMPRISING A MUCONOPEPTIDE

BACKGROUND OF THE INVENTION

Facial and other skin lines and wrinkles develop through a combination of aging, heredity, muscle action, sun damage and gravity. Facial and other skin expressions are made by strong muscle contractions, and over time, create skin wrinkles such as forehead lines, crow's feet and the vertical creases between the eyes. Wrinkles mostly result from a strong muscular contraction or from a prolonged time in this position. At the cellular level, the fibroblast cells synthesizing the extracellular matrix and collagen that are located along the tension lines could under the effect of muscular contractions develop particular contractile properties related to striated muscle.

The junction between a nerve and striated muscle constitutes the neuromuscular plates, upstream of which is the afferent nerve pathway, known as the motor neuron.

Muscle contraction is caused by acetylcholine, a neurotransmitter. Acetylcholine is released by the nerve that stimulates the muscle. It is known that the skin muscles of the face are under control of motor nerve afferences, and the hypoderm contains fine, flat sheets of striated muscle called the panniculus carnosus that constitute muscle tissue.

Today such mimic and age-related wrinkles are often treated with Botox (*Botulinum toxin* A, produced by the pathogenic microorganism *Clostridium botulinum*). Botox acts by preventing the release of acetylcholine. This toxin temporally paralyzes the muscle and inhibits contraction. Absences of contractions prevents wrinkles and induces a smooth and rejuvenated skin. Such toxins act as proteases, more specifically zinc endopeptidases targeting the neuronal cytosol: Botox B, D and F, as well as tetanus toxin produced by the *Clostridium tetani* pathogenic microorganism attack specifically VAMP (also called synaptobrevin)—a protein of synaptic vesicles; Botox A and E cleave SNAP-25 and Botox C acts on syntaxin—both proteins of the presynaptic membrane (See for example Proc. West. Pharmacol. Soc. 43: 71-74, 2000.

Botox is injected locally in tissues which are thereby paralyzed. The muscles at the eyes or at the forehead don't operate any more, making the apparition of a forehead wrinkle difficult if not impossible. However, the fact that the treatment with subcutaneously injected Botox has to be conducted by a physician, its consequently high costs and its extremely high toxicity constitute considerable disadvantages. Its effectiveness lasts from 3 to 6 months, whereupon the treatment has to be repeated.

It is known from the European patent applications EP 2123673 and EP 1180524 under the name of Lipotec that peptides comprising an amino acid sequence derived from the amino acid sequence of the protein SNAP25 can compete with SNAP 25 by mimicking its IM-terminal end and thus interfering in the SNARE complexes. If the SNARE complexes are destabilized, the synaptic vesicles cannot release acetylcholine efficiently and muscle contraction can be altered.

The mechanism of action of these peptides is similar to that of botulinum toxins focusing on inhibition of neuronal exocytosis of acetylcholine.

El Far Oussama and col. In Patent application WO 2011/448441 in the name of INSERM describes direct molecule interaction between VATPase and SNARE synaptobrevin (VAMP2). Soluble peptides with sequence corresponding to a portion of a VATPase subunit have the property to interfere with the neurotransmitter release.

Patent application WO 2009/012376 IN THE NAME OF University of OHIO STATE RES FOUND refers to opioid receptors that have been identified in peripheral processes of sensory neurons. Peptides have been used as delta opioid receptor agonists. This binding with the receptors inhibits the release of GABA from the nerve terminal, reducing the inhibitory effect of GABA on dopaminergic neurons.

Other peptides that are able to acts in a manner similar to Waglerin 1, a snake venom protein, acting at the post-synaptic membrane, as antagonist of the muscular nicotinic acetylcholine receptor are described in patent application WO 2006/047900 in the name of Pentapharm.

Moreover, cell membranes comprise numerous ion channels. Molecules acting as calcium channels inhibitors are for example described in the US patent application 2008/0050318 in the name of L'OREAL.

These calcium channels can be found in human fibroblasts, see for example J. Biol. Chem 267; 10524-10530, 1992 and Science 230 1024-1026, 1988.

Original peptides isolated from the venom of marine snails belonging to the family of mu-conotoxin or mu-conopeptides and acting as sodium channel inhibitors have been described in patent applications WO 2004/099238, WO 2002/07678, US 2003/050234 or WO 2007/054785. Voltage sensitive channels are key components for generating action potentials in electrically excitable cells by forming the action potential upstroke. A great diversity of sodium ion channel types and sub-types exist. All of them are voltage-sensitive sodium channel (VSSC) which open and then close in response to membrane depolarization.

The mu-conopeptides from venoms of the marine snails are able to block VSSC by blocking directly action potentials in sciatic and olfactory nerves of mouse and pike, for example. The resulting pharmacological effect consists in a block of conductance, leading to loss of function of neuromuscular system as described in the patent application WO 2007/054785 in the name of ATHERIS.

Based on their susceptibility to be blocked by tetrodotoxin (TTX), VGSCs can be divided into tetrodotoxin sensitive (TTX-S) and TTX-resistant (TTX-R) classes. These include the neuronal TTX-S type 1/Nav1. 1, lilNav1. 2 III/Nav1. 3, PN1/Nav1.7 and PN4/Nav1.6, and the skeletal muscle TTX-S u1/Nav1.4.

Mu-conopeptides target a variety of voltage sensitive sodium channel, blocking primarily the Navl.4 channel.

To date, no inhibitory activity on sodium channel for cosmetic application has been described or suggested for these peptides.

SUMMARY OF THE INVENTION

We demonstrate that mu-conopeptides make it possible to neutralize the formation of the expression skin wrinkles on human faces. They can neutralize the effects of microtensions on the skin by relaxing dermal contractile fibroblasts which are assumed to be involved in the genesis of expression wrinkles.

More particularly mu-conopeptide CnIIIC, a 23-residue peptide with three disulfide bridges, blocker of voltage-gated sodium channels particularly the muscular subtype NaV1.4, formulated as a topical product was found to induce specific actions.

For example, CnIIIC reduces facial lines and wrinkles developed through aging, heredity, sun damage and gravity. These facial lines or wrinkles are characterized by furrows at the periphery of the orifices, namely the nose (nasogenic furrows), the mouth (perioral lines and bitterlines), the forehead and the eyes (crow's feet) around which the facial muscles are located.

The invention consists in a cosmetic composition comprising as an active substance a cosmetically effective amount of at least one mu-conotoxin peptide comprising the amino acid sequence: Xaa1-Xaa2-Cys-Cys-Xaa3-Xaa4-Xaa5-Xaa6-Xaa7-Cys-Xaa8-Xaa9-Xaa10-Xaa11-Cys-Xaa12-Xaa13-Xaa14-Xaa15-Xaa16-Cys-Cys-Xaa17 [SEQ ID NO: 1]

A biologically active fragment thereof, a salt thereof, a combination thereof and/or variants thereof, and wherein Xaa1 is any N-modified amino acid, Xaa2 is glycine, Xaa3 is any acidic amino acid or any of its amide form, Xaa4 is glycine, Xaa5 is proline or 3-hydroxyl-proline, Xaa6 is any basic amino acid, Xaa7 is glycine, Xaa8 is any non-aromatic hydroxyl amino acid, Xaa9 is any non-aromatic hydroxyl amino acid, Xaa10 is any basic amino acid, Xaa11 is any aromatic amino acid, Xaa12 is any basic amino acid, Xaa13 is any acidic amino acid or any of its amide form, Xaa14 is any basic amino acid, or any sulfur-containing amino acid, Xaa15 is any hydrophobic or apolar amino acid, or any non-aromatic hydroxyl amino acid, Xaa16 is any basic amino acid, Xaa17 is absent or is any apolar amino acid, or an amide group, optionally in combination with cosmetic acceptable carriers, diluents and/or adjuvants.

DETAILED DESCRIPTION OF THE INVENTION

Figure 1:
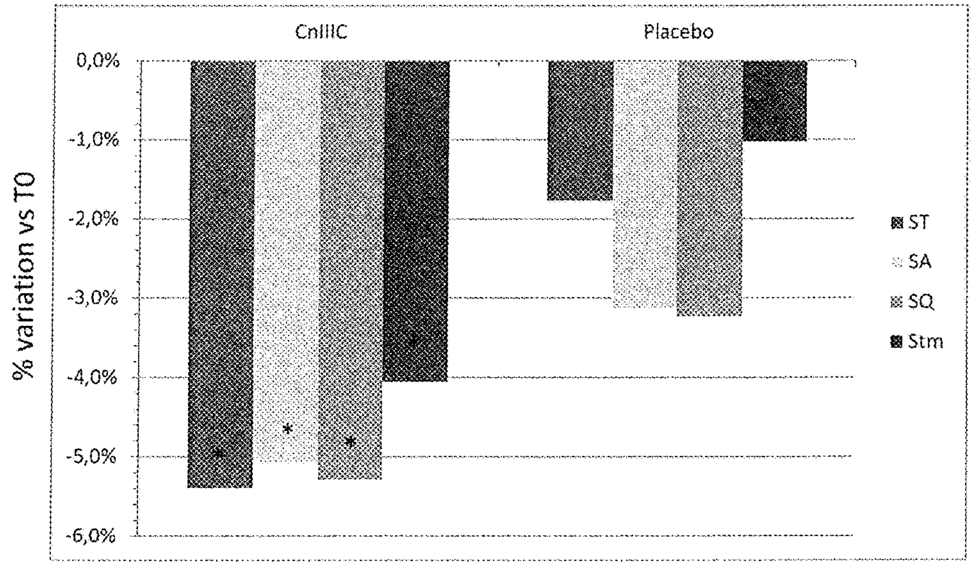
FIG. 1 shows the effects of CnIIIC on Crow's feet wrinkles and rugosity.

In one embodiment in the composition of the invention the mu-conotoxin peptide does not comprise at least one amino acid consisting of amino acids Xaa3, Xaa4, Xaa5, Xaa6 and Xaa7, or any combination thereof.

In one embodiment in the composition of the invention the mu-conotoxin peptide does not comprise at least one amino acid consisting of amino acids Xaa8, Xaa9, Xaa10 and Xaa11, or any combination thereof.

In one embodiment in the composition of the invention the mu-conotoxin peptide does not comprise at least one amino acid consisting of amino acids Xaa12, Xaa13, Xaa14, Xaa15 and Xaa16, or any combination thereof.

In one embodiment in the composition of the invention the N-modification of amino-acid Xaa1 in the mu-conotoxin peptide is selected from the group comprising acetylation, formylation, myristoylation or amidation;

Xaa3 and Xaa13 are independently selected from the group comprising aspartic acid (Asp), asparagine (Asn), glutamic acid (Glu), glutamine (Gin) and pyroglutamic acid (pGlu or Z);

Xaa6, Xaa10, Xaa12 and Xaa16 are independently selected from the group comprising arginine (Arg), lysine (Lys) and histidine (His);

Xaa8 and Xaa9 are independently selected from the group comprising serine (Ser) and threonine (Thr);

Xaa11 is selected from the group comprising phenylalanine (Phe), tyrosine (Tyr), and tryptophane (Trp);

Xaa14 is selected from the group comprising arginine (Arg), lysine (Lys) and histidine (His), cysteine (Cys) and methionine (Met);

Xaa15 is selected from the group comprising glycine (Gly), alanine (Ala), valine (Val), leucine (Leu) and isoleucine (He), serine (Ser), threonine (Thr), methionine (Met), cysteine (Cys) and proline (Pro);

Xaa17 is selected from the group comprising glycine (Gly), alanine (Ala), valine (Val), leucine (Leu), isoleucine (He), threonine (Thr), methionine (Met), phenylalanine (Phe) and proline (Pro).

In one embodiment in the composition of the invention in the mu-conotoxin peptide, Xaa1 is pyroglutamate (pGlu), In one embodiment in the composition of the invention, in the mu-conotoxin peptide, the amino acid sequence is pGlu-Gly-Cys-Cys-Asn-Gly-Pro-Lys-Gly-Cys-Ser-Ser-Lys-Trp-Cys-Arg-Asp-His-Ala-Arg-Cys-Cys-amide [SEQ ID NO: 2], a biologically active fragment thereof, a salt thereof, a combination thereof and/or variants thereof.

The term "variant" refers to a peptide having an amino acid sequence that differ to some extent from a native sequence peptide, that is an amino acid sequence that vary from the native sequence by conservative amino acid substitutions, whereby one or more amino acids are substituted by another with same characteristics and conformational roles. The amino acid sequence variants possess substitutions, deletions, side-chain modifications and/or insertions at certain positions within the amino acid sequence of the native amino acid sequence.

In one embodiment in the composition of the invention the mu-conotoxin peptide is Arginine, lysine polypeptide (INCI name: pyroglutamyl s-mu-conotoxin CnIIIc amide acetate), CAS Number: 937286-43-6 (renumbered 936616-33-0), Molecular formula $C_{92},H_{139},N_{35},O_{28},S_6$ acetate salt (molar mass 2376 g/mol.).

In one embodiment the at least one mu-conotoxin peptide is present in an amount ranging from $0.05.10^{-6}$ to $1.10^{-3}$% by weight of the total weight of the composition In one embodiment the at least one mu-conotoxin peptide is present in an amount ranging from $0.05.10^{-6}$ to $1.10^{-4}$% by weight of the total weight of the composition.

In a further embodiment it is present in an amount ranging from $0.05.10^{-4}$ to $0.1.10^{-4}$% by weight of the total weight of the composition.

In a further embodiment it is present in an amount ranging from $0.1.10^{-4}$ to $1.10^{-4}$% by weight of the total weight of the composition.

In a further embodiment it is present in an amount ranging from $0.05.10^{-2}$ to 1 mg/kg of the total weight of the composition.

In a further embodiment it is present in an amount ranging from 0.01 to 0.1 mg/kg of the total weight of the composition.

In a further embodiment it is present in an amount ranging from 0.1 to 1 mg/kg of the total weight of the composition.

In an embodiment the at least one mu-conotoxin peptide is present in a molar concentration ranging from 21 nM to 4.2 μM.

In an embodiment the at least one mu-conotoxin peptide is present in a molar concentration ranging from 0.05 μM to 0.50 μM.

In a further embodiment it is present in a molar concentration ranging from 0.10 μM to 0.30 μM.

In a further embodiment it is present in a molar concentration ranging from 0.25 μM to 0.35 μM.

In one embodiment, the composition of the invention further comprises a cationic surfactant.

Surprisingly, the cationic surfactant enhances the cutaneous permeation of the mu-conotoxin peptide.

The cationic surfactant is chosen amongst the cationic surfactant that could be used in cosmetic compositions, like pH-dependent primary, secondary, or tertiary amines or permanently charged quaternary ammonium cations like alkyltrimethylammonium salts, Benzalkonium chloride, Dioctadecyldimethylammonium bromide or cetearyl alcohol and behentrimonium Methosulfate.

In one embodiment the cationic surfactant is present in an amount ranging from 1 to 6% by weight of the total weight of the composition.

In a further embodiment it is present in an amount ranging from 3 to 5% by weight of the total weight of the composition.

The anti-wrinkle effect could be observed from 5 minutes after the application of the composition onto the skin.

In one embodiment it could be observed from 10 minutes from the application.

In one embodiment it could be observed from 20 minutes from the application.

In one embodiment it could be observed from 20 minutes to 48 hours from the application.

The anti-wrinkle effect is observed with conventional methods know from the man skilled in the art like analysis of the skin surface carried out by calculating the standard roughness parameters.

The invention also consists in the use of a composition of the invention, to prevent and/or treat the intrinsic and extrinsic signs of skin aging: wrinkles, fine lines, discontinuities and roughness of the skin, skin sagging, skin spots and/or loss of brightness of complexion.

In one embodiment the use of a composition of the invention is to improve the mechanical properties of the skin, in terms of tonicity and/or firmness and/or elasticity of the skin.

In one embodiment the use of a composition of the invention is to improve the density of the dermis and epidermis, to give or restore volume to the dermis and epidermis.

In one embodiment the invention is a cosmetic process for treating the wrinkles comprising topically application to the skin of a composition of the invention.

More particularly it consists of applying such a composition to the areas of the face marked with wrinkles.

The invention also consists in a cosmetic process for treating wrinkles and fine lines comprising topically applying to the skin a composition comprising as an active substance and in an amount ranging from $0.05\times10^{-6}$ to $1\times10^{-3}$ percent by weight of the total weight of the composition, the mu-conotoxin peptide of sequence SEQ ID NO:1 or a variant thereof, said variant having one substituted amino acid and/or at least one deleted amino acid.

In one embodiment, the active substance is in an amount ranging from $0.05\times10^{-6}$ to $1\times10^{-4}$ percent by weight of the total weight of the composition.

In one embodiment, the mu-conotoxin peptide comprised in the composition used in the cosmetic process of the invention is a variant of the mu-conotoxin peptide of sequence SEQ ID NO:2, said variant having one substituted amino acid and/or at least one deleted amino acid and the N-terminal amino acid being a N-modified amino acid.

The term "variant" refers to a peptide which sequence derives from the sequence of a parent mu-conotoxin peptide of sequence SEQ ID NO:1 or SEQ ID NO:2, said peptide having the same biological activities as those of the parent mu-conotoxin. In a further embodiment, the variant of the mu-conotoxin peptide of sequence SEQ ID NO:2 is selected in the group comprising or consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21.

In one embodiment, the N-terminal amino acid of the variant of the mu-conotoxin peptide of sequence SEQ ID NO:2 comprised in the composition used in the cosmetic process of the invention is a Lysine (K) residue.

In one embodiment, the Lysine (K) residue of the variant of the mu-conotoxin peptide of sequence SEQ ID NO:2 comprised in the composition used in the cosmetic process of the invention is Xaa1.

In one embodiment, the N-modification of the variant of the mu-conotoxin peptide of sequence SEQ ID NO:2 comprised in the composition used in the cosmetic process of the invention is selected from the group comprising myristoylation, decanoylation, laurylation, stearylation, oleylation and palmitoylation.

In a further embodiment, the Lysine (K) residue is Xaa1 and the N-modification is selected from the group comprising myristoylation, decanoylation, laurylation, stearylation, oleylation and palm itoylation.

In one embodiment, an anti-wrinkle and fine lines effect is observed for 20 minutes to 48 hours, or longer from the topical application of the composition to the skin. In one embodiment, a 5% reduction in wrinkles and fine lines appearance is visible after 2 hours of topical application of the composition to the skin.

In one embodiment the composition of the invention is suitable for topical application to the skin and thus contains a physiologically acceptable medium, i.e., a medium that is compatible with the skin.

In one embodiment the composition may be in any presentation form normally used in cosmetics, and it may, for example, be in the form of an optionally gelled aqueous solution, a dispersion of the lotion type, optionally a two-phase lotion, an emulsion obtained by dispersing a fatty phase in an aqueous phase (O/W emulsion) or conversely (W/O emulsion), or a triple emulsion (W/O/W or 0/W/O emulsion) or a vesicular dispersion of ionic and/or nonionic type. These compositions are typically prepared according to the usual methods.

In one embodiment the composition is in the form of a cream, an ointment, a milk, a lotion, a serum, a paste or a foam.

In one embodiment the composition of the invention comprises one or more additional active ingredient selected from brightening, anti-redness agents, sunscreens and UV organic or inorganic filters, hydration, moisturizing, humectants, exfoliants, anti-wrinkle, anti-ageing, slimming, antiacne, anti-inflammatory, antioxidant, radical scavenger, self tanning, depilation or shave, hair growth moderator, tightening agents, peptides and vitamins.

In one embodiment the composition of the invention may comprise at least one adjuvant chosen from adjuvants such as hydrophilic and lipophilic gelling agents, hydrophilic and lipophilic active agents, preserving agents, antioxidants, solvents, fragrances, fillers, screening agents, pigments, odor absorbers and dyestuffs. The adjuvant is present in an amount ranging, for example, from 0.01% to 50% by weight relative to the total weight of the composition.

In one embodiment the composition of the invention may also comprise at least one agent chosen from UVA-active and UVB-active organic and mineral photoprotective agents.

In one embodiment the composition of the invention is used with a device to enhance the permeation.

In a further embodiment the device is a ionophoresis device.

EXAMPLES

The product referenced as CnIIIC in the following examples is:

```
                                        [SEQ ID No 2]
pGlu-Gly-Cys-Cys-Asn-Gly-Pro-Lys-Gly-Cys-Ser-Ser-

Lys-Trp-Cys-Arg-Asp-His-Ala-Arg-Cys-Cys-amide
```

It is also referred as Arginine, lysine polypeptide (INCI name: pyroglutamyl s-mu-conotoxin CnIIIc amide acetate), CAS Number: 937286-43-6 (renumbered 936616-33-0), Molecular formula $C_{92}$, $H_{139}$, $N_{35}$, $O_{28}$, $S_6$ acetate salt (molar mass 2376 g/mol.). It is used as a mother solution which concentration is 10 μM. The mother solution is added in the final compositions in an amount ranging from 1 to 3%.

Example 1

Anti-Age Soothing Day Cream Ingredients % by Weight
Isopropyl palm itate: 20%
Cetearyl alcohol: 10%
Cetyl alcohol: 5%
Ceteareth-33: 10%
Dimethicone: 5%
Parfume: 0.5%
Preservatives: 0.5%
CnIIIC: $0.6.10^{-4}$% (3% of the mother solution)
Water: QSP100

Example 2

Cream for Mature Skin
Carbomer: 0.2%
Glycerin: 3.5%
Potassium sorbate: 0.1%
Steareth 10: 1.5%
Cetearyl alcohol dicetyl phosphate: 3.5%
Dimethicone: 2.0%
Sorbitan sterarate: 0.4%
Sodium hydroxyde: 0.2%
CnIIIC: $0.2.10^{-4}$% (1% of the mother solution)
Water: QSP 100

Example 3

Ammonium Acryloyldimethyltaurate/VP Copolymer: 0.5%
Glycerin: 3.0%
Dipropylene Glycol: 4.0%
Stearyl Alcohol: 4.0%
Jojoba Esters: 3.0%
Behentrimonium Methosulfate (and) Cetyl Alcohol (and) Butylene Glycol: 4.0%
Dimethicone: 5.0%
Dimethyl Isosorbide: 5.0%
Phenethyl Alcohol (and) Ethylhexylglycerin: 2.0%
CnIIIC: $0.6.10^{-4}$% (3% of the mother solution)
Water: QSP 100

Example 4

Quantification of the Anti-Wrinkles Effect on Humans

The principle is to quantify the micro cutaneous relief by analyzing the deformation of networks of high-contrast lines projected on the surface under investigation on healthy human volunteers.

Parameters are quantified on a series of profiles perpendicular to the lines and wrinkles in the measurement zone.

The product was conceived for once daily application. We aimed at assessing the effect of the topical product versus placebo through an in vivo evaluation protocol, performed using a skin bioengineering method, namely in vivo fringe projection. The concentration of the tested composition is 0.6 mg/kg so 0.6 $10^{-4}$% (w/w).

The measurements are carried out on both half of the face for the peribuccale, the crow's foot, and forehead wrinkles. They are taken using an optical system dedicated to the metrology of the relief of surfaces. The analysis of the cutaneous topography of the surface is carried out by calculating the parameters of standard roughness.

The protocol was conducted as a double-blind, active versus placebo trial, on 30 subjects over an eight hours period, during which volunteers were checked three times (TO, T2h and T8h), both clinically and for the changes of the cutaneous relief. The measurements were made using an optical system dedicated to the relief of metrology surfaces. This system includes a sensor associated with a projector and a CCD camera highresolution—Dermatop system (EoTech, France)—associated with the acquisition software Optocat (EoTech, France).

The average axial and lateral resolutions are of the order of 10 microns.

At the end of the trial, tolerability was good. The enrolled volunteers expressed their full satisfaction regarding the product under study. A single acquisition is made by area. The visualization on the screen of the initial acquisition (TO) allows the correct repositioning of the Tn area.

Analysis

Analysis of the skin surface is carried out by calculating the standard roughness parameters. These parameters are extracted from an area of 30×40 mm (12 cm2). Analysis of data obtained by fringe projection, on the study areas is performed through the analysis system and Toposurf Optocat.

Profile Parameter

SPt: Maximum amplitude of relief (mm).

For crow's feet, decreasing SPt means a reduction of main wrinkle. This parameter is sensitive to artifacts.

SPa: Average roughness (mm). It means changes in amplitude of the relief of the surface studied. A decrease in this parameter means a surface smoothing and a reduction of wrinkles and fine lines.

SPQ or SQ: Average of the dispersion of changes in relief (mm) using square deviation. Same interpretation as Spa even if this parameter is less sensitive to artifacts.

Morphology Parameters

Wrinkles and fine lines are detected after the use of multiple filters and correction polynomial to remove the shape and flatten the study area.

Mean area of the wrinkles ($mm^2$) This parameter corresponds to the mean area of objects (lines and wrinkles) detected in the study area.

Average volume of wrinkles ($mm^3$). This parameter corresponds to the average volume of objects (lines and wrinkles) detected in the study area.

Average depth of wrinkles (mm). This parameter corresponds to the average depth of objects (lines and wrinkles) detected in the study area.

Figure 2:
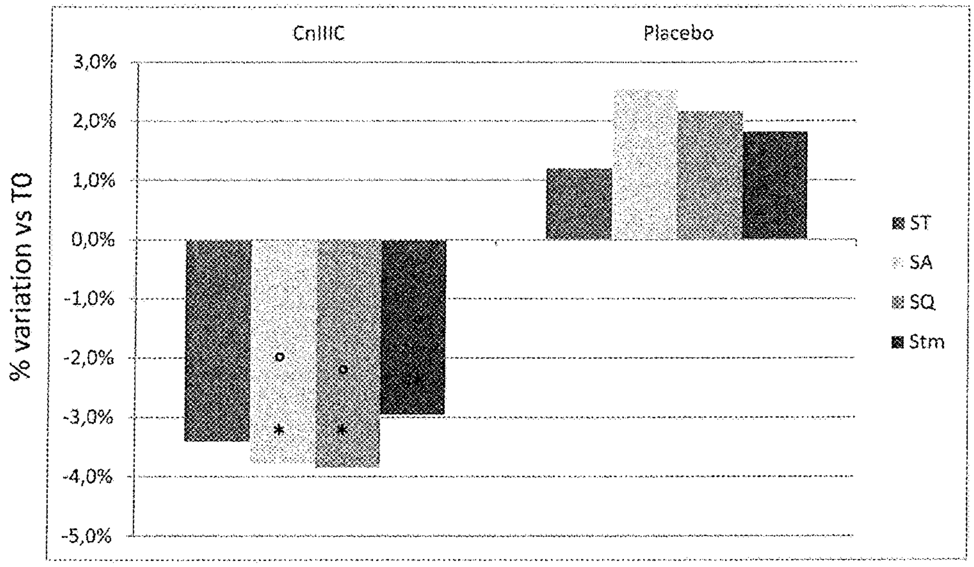
FIG. 2 shows the effects of CnIIIC on forehead wrinkles and rugosity.
Figure 3:
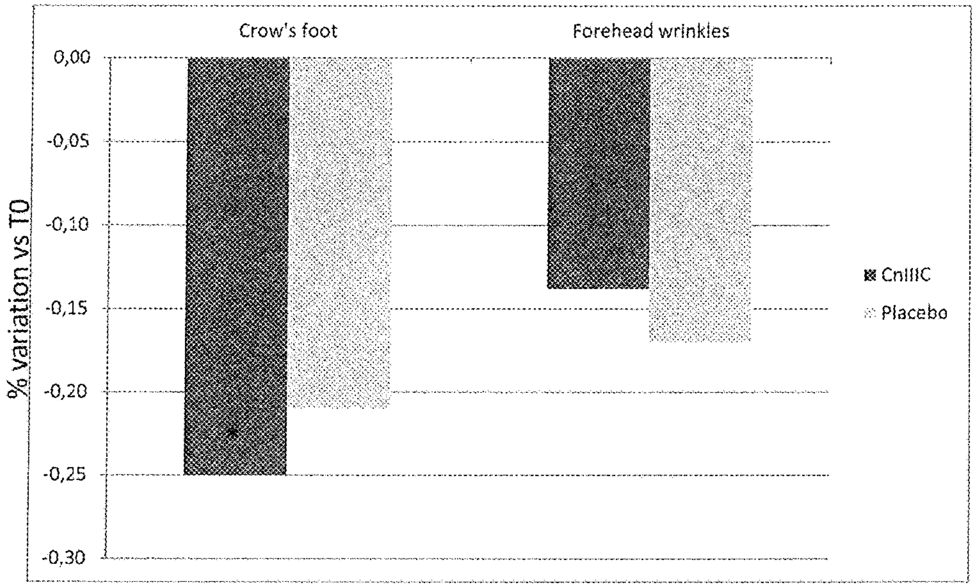
FIG. 3 represents a comparison of the effects of CnIIIC on Crow's feet and forehead wrinkles.

The results are shown in FIGS. 1, 2 and 3:

FIG. 1 shows effect of CnIIIC on Crow's feet wrinkles and rugosity.

FIG. 2 shows effect of CnIIIC on forehead wrinkles and rugosity.

FIG. 3 represent a comparison of the effects of CnIIIC on Crow's feet and forehead wrinkles.

In each figure:

*p<0.05 student. Statistically significant vs TO in favor CnIIIC.

° p<0.05 Wilcoxon. CnIIIC statistically different from placebo.

The results as shown in FIGS. 1, 2 and 3 demonstrate that the anti-wrinkles effect is significant. CnIIIC significantly reduces wrinkles & fine lines appearance of Crow's feet according to clinical evaluation: 5% after 2 hours of application on forehead and crows feet and more than 8% against placebo for SA parameters.

Example 5

In Vitro Experiments on Sodium Current Recorded from HEK Cells by Patch-Clamp

Patch-clamp current recordings were performed in HEK 293 cells stably expressing the rat skeletal muscle Na channel a subunit (μ1, Nav1.4) (Yamagishi et al., 1997, Biophysical Journal, vol. 73, pp. 195-204). These cells display robust Na currents (>2 nA), are sensitive to saxitoxin (STX) and derivatives (Velez et al., 2001, Toxicon, vol. 39, pp.929-935), and have a small size (diameter <20 μm), allowing an appropriate control of the holding potential.

Whole-cell patch-clamp recordings (Hamill et al., 1981, Pfligers Arch. vol.391, pp.85-100.) were performed at room temperature (20-22° C.) on HEK 293 cells stably expressing Nav1.4 channels. Patch pipettes made from borosilicate glass and pulled on a P-97 puller (Sutter Instrument Company, Novato, Calif.) had a 1.5-3.0 MΩ tip resistances when filled with internal physiological solution. Membrane currents were recorded using an Axopatch 200-B patch-clamp amplifier (Axon Instruments, Union City, Calif.). Peak sodium currents were elicited by 10-ms depolarizing pulses from a holding voltage of −100 to −10 mV. A P/4 protocol was used to subtract linear capacitative and leak currents. Membrane currents were filtered with an integrated 8-pole low-pass Bessel filter at 10 kHz. The filtered signals were digitized by a 12 bit A/D converter (Digidata 1200B, Axon Instruments) and stored using pCLAMP software (Axon Instruments). Recordings were analyzed using Origin 7 software (OriginLab Corp., Northampton, Mass.).

The cells were continuously perfused at 1 ml $min^{-1}$ with a control external solution containing (in mM): 70 NaCl, 70 tetraethylammonium chlorhidrate, 5 KCl, 3 CaCl2, 1 MgCl2, 10 mM glucose, 10 HEPES (pH 7.4). The patch pipette contained (in mM) 140 CsF, 5 NaCl, 1 MgCl2, 10 EGTA, 10 HEPES buffer (pH 7.2). Na currents were recorded under control conditions and after perfusion with 1 μM of μ-conotoxin CnIIIA (μ-CnIIIA), or a variant thereof or with saxitoxin diacetate (STX) (Sigma-Aldrich Chemical Corp).

The results are illustrated in table below:

| Mu-conopeptides Id | Block of NaV1.4 at 1 microM | | | |
|---|---|---|---|---|
| | Onsets | SEM_Onsets | Block (%) | SEM_Block (%) |
| SEQ ID NO: 2 | 266 | 45 | 96.3 | 0.7 |
| SEQ ID NO: 4 | 173 | 12 | 90.8 | 3.2 |
| SEQ ID NO: 5 | 130 | 13 | 96.4 | 0.4 |
| SEQ ID NO: 6 | 72 | 7 | 95.3 | 0.2 |
| SEQ ID NO: 7 | 279 | 24 | 91.3 | 2.2 |
| SEQ ID NO: 8 | 121 | 7 | 97.5 | 0.1 |
| SEQ ID NO: 9 | Not available | | | |
| SEQ ID NO: 10 | 247 | 6 | 99.2 | 0.9 |
| SEQ ID NO: 11 | 112 | 30 | 94.9 | 1.3 |
| SEQ ID NO: 12 | 34 | 5 | 95.3 | 0.6 |
| SEQ ID NO: 13 | 56 | 6 | 97.1 | 0.1 |
| SEQ ID NO: 14 | 976 | 117 | 93.6 | 1.1 |
| SEQ ID NO: 15 | 1129 | 213 | 91.0 | 3.0 |
| SEQ ID NO: 16 | 694 | 39 | 90.0 | 6.0 |
| SEQ ID NO: 17 | 1372 | 158 | 93.2 | 1.6 |
| SEQ ID NO: 18 | 185 | 9 | 95.2 | 0.3 |
| SEQ ID NO: 19 | 261 | 13 | 94.9 | 0.3 |

All experiments were performed in triplicates, except for mu-conopeptides of SEQ ID NO: 2, 14 and 17 where quadriplicates were performed.

The results demonstrate the ability of CnIIIC (SEQ ID NO:2) to block expressed Nav1.4 channels, -i.e. to reduce the sodium flux to less than 4%-. The anti-wrinkles and fine lines effect of CnIIIC observed in example 4 relies on the ability of CnIIIC to block the voltage-gated sodium channel Nav1.4 isoform.

By screening the Nav1.4 blocking activity of variants of CnIIIC, the inventors identified several peptides usable in the cosmetic process according to the invention.

Hence, the results in table above also demonstrate the ability of all the variants derived from SEQ ID NO:2 to block the voltage-gated sodium channel Nav1.4 isoform, except for the peptide of SEQ ID NO: 9 for which not data was available. Among all the variants tested, those having a lysine residue at position Xaa1 and wherein a fatty acid was covalently linked to said lysine have the greatest blocking activity on Nav1.4 channel (see SEQ ID NO: 8, 10 and 13).

Example 6

Anti-Age Cream (Ingredients % by Weight)

Glycerin: 3%

Dimethyl Isosorbide: 5%

Butylene Glycol: 5%

Tromethamine: 0.5%

Citric Acid: 0.2%

Phenoxyethanol & Caprylyl Glycol & PotassiumSorbate & Water & Hexylene

Glycol: 1%

Beeswax: 3%

Olive Squalane: 2%

Octyl Palm itate: 4%

Octyldodecyl Stearoyl Stearate: 2%

Cetyl Alcohol: 1%

Stearyl Alcohol: 1%

Sucrose Polystearate: 0.5%

Glyceryl Stearate & PEG-100 Stearate: 1.8%

Caprylic/Capric/Myristic/Stearic Triglyceride: 4.2%

Dimethicone & Polysilicone-11: 10%

Ammonium Acryloyldimethyltaurate/VP Copolymer: 0.4%

Polyacrylate-13 & Polyisobutene & Polysorbate 20: 1

Alum inumStarch Octenylsuccinate: 1.5%

Cocos Nucifera (Coconut) Oil: 2%

CnIIIC: $6\times10^{-4}$% (5% of the mother solution)

Water: QSP100

Example 7

Bentonite & Xanthan Gum: 2%

Steareth-21: 2%

Dimethyl Isosorbide: 5%

Butylene Glycol: 3%

Sorbic Acid: 0.2%

Adipic Acid/Neopentyl Glycol Crosspolymer & Water & Aminodimethicone & Dimethicone & Hydroxypropyl Methylcellulose & VP/VA Copolymer: 5%

Polysilicone-11 & Water & Laureth-12 & Phenoxyethanol & Ethylhexylglycerin: 15%

Dimethicone & Cyclopentasiloxane & Polysilicone-11: 24%

Sodium Citrate: 0.3%

Citric Acid: 0.1%

Sodium Acrylate/Sodium Acryloyldimethyl Taurate Copolymer & Isohexadecane &

Polysorbate 80: 1.5%

Phenoxyethanol: 0.5%

Polymethylsilsesquioxane: 2%

CnIIIC at 50pM: 5%

Water: QSP100

Example 8

In Vitro Passive and Iontophoretic Delivery of CnIIIC and Variants on Skin

The aim of the study was to evaluate the passive diffusion of CnIIIC and variants thereof for short and long durations i.e. 5, 15, 120 and 480 minutes as well as improving their delivery using short duration (5 and 15 minutes) iontophoretic transport experiments from aqueous solution ranging from 40 μM to 0.1 mM using low current intensities i.e. 0.25 and 0.5 mA/cm2. The evaluation of CnIIIC and variants thereof deposition and biodistribution in skin was quantified using UHPLC-MS/MS.

Chemicals

Acetonitrile and Formic acid of HPLC/UPLC grade were purchased from Biosolve BV (Netherlands). Dulbecco's Phosphate Buffered Saline without calcium and magnesium chloride was obtained from Life Technologies Corporation (UK). 2-methyl butane (isopentane) was purchased from Acros Organics (Belgium). Acetic acid, sodium chloride, agarose, Tween 80 were provided by Sigma-Aldrich (Switzerland). All solutions were prepared using deionised water. All other chemicals were at least of analytical grade. Porcine skin of a thickness of 2.0 mm was used for the evaluation of CnIIIC and variants thereof.

Experimental Protocols

Skin Deposition Experiments

Donor solution consisted of 0.1 mM or 40 μM CnIIIC and variants thereof in water with Tween 80 (0.1%) and 20 mM HEPES (pH=5.6 for CnIIIC and pH=5.3 or 5.4 for CnIIIC variants). Receptor compartment solution consisted of PBS buffer (pH=7.4; 11 mL). Saline bridges were used to avoid ion competition. Passive and iontophoretic (current density of 0.25 mA/cm2 or 0.5 mA/cm2) deposition of CnIIIC and variants thereof were evaluated after 5 and 15 minutes using UPLC-MS/MS. After the given application time, any remaining formulation was removed from the skin surface and tape-stripped 5 times to remove any residue. Then, the skin samples were cut into small pieces and extracted with the corresponding extraction medium.

Skin Extraction Conditions

For CnIIIC, skin extraction was performed by placing each sample in 5 mL of 0.1% acetic acid solution containing Tween 80 (0.1%) and stirring for 4 hours; the supernatant was filtered using nylon filters with a pore size of 0.22 μm. Slightly different conditions were used for the more lipophilic CnIIIC variants. The skin extraction procedure involved stirring skin samples in a 5 mL mixture of water-acetonitrile (50/50) containing formic acid (0.1%) and Tween 80 (0.1%) for 4 hours; in this case, extraction samples were filtered using PVDF filters with a pore size of 0.22 μm.

Skin Biodistribution Experiments

Biodistribution of the different CnIIIC and variants thereof was evaluated using a buffered aqueous solution of CnIIIC and variants thereof at a concentration of 40 μM. An iontophoretic current density of 0.25 mA/cm$^2$ was applied for 5 minutes; passive transport was investigated using the same set-up and conditions but in the absence of current. After the completion of the experiment, the set-up was carefully dismantled and the skin surface cleaned as described previously. Then, the skin samples were snap frozen in isopentane cooled with liquid nitrogen. Skin lamellae with a thickness of 20 μm were obtained using a cryotome (Microm HM 560 cryotome), pooled and extracted as described above.

Skin Extraction Conditions

The same extraction conditions were deployed for the skin biodistribution studies as described above except that the volumes and duration of extraction were decreased. For the stratum corneum (0-20 μm) and viable epidermis (20-140 μm), 1.5 mL of extraction medium was used while for the dermis, 2.5 mL of the appropriate extraction medium was used. Extraction was performed for 4 hours.

Analytical Methods

UHPLC-MS/MS was used to quantify CnIIIC and variants thereof using a C4 column (300 Å, 1.7 μm, 2.1×50 mm) and pre-column (300 Å, 1.7 μm, 2.1×5 mm) from Waters. The column temperature for the analysis was maintained at 45° C. A gradient separation method was used with Mobile Phase A—water containing formic acid (0.1%) and Mobile Phase B—acetonitrile with formic acid (0.1%) with a flow rate of 0.3 m L/min. The injection volume was 5 μL. The respective gradients used to quantify CnIIIC and variants thereof are described below:

CnIIIC: 5% B to 50% B in 2.5 min

CnIIIC variants: 10% B to 55%B in 2.5 min or 10% B to 70%B in 2.5 min.

CnIIIC and CnIIIC variants deposition

Results related to the average deposited amounts of CnIIIC (SEQ ID NO:2) and variant (SEQ ID NO: 8) in skin as a function of experiment duration and current application are illustrated in tables below:

| | 120 min., 0.1 mM | | 480 min., 0.1 mM | |
|---|---|---|---|---|
| | CnIIIC (Seq ID NO: 2) Passive | SEQ ID NO: 8 | CnIIIC (Seq ID NO: 2) Passive | SEQ ID NO: 8 |
| Mean | 1637 | 1473 | 2321 | 3641 |
| Standard deviation | 608 | 834 | 1161 | 1367 |

Amounts are expressed as mean ± SD (ng/cm$^2$).

Regarding passive delivery, increasing the duration of application resulted in an increase in the deposited amounts of CnIIIC and variants thereof in skin. At a concentration of 0.1 mM, the highest deposited amounts were found after 8 h, for all CnIIIC variants.

| | 5 min., 0.1 mM, (+/−)* 0.5 $mA/cm^2$ | | | |
|---|---|---|---|---|
| | CnIIIC (Seq ID NO: 2) | | SEQ ID NO: 8 | |
| | Passive | Iontophoresis | Passive | Iontophoresis |
| Mean | 781 | 2567 | 576 | 7271 |
| Standard deviation | 170 | 1055 | 348 | 1898 |
| | 15 min., 0.1 mM, (+/−)* 0.5 $mA/cm^2$ | | | |
| | CnIIIC (Seq ID NO: 2) | | SEQ ID NO: 8 | |
| | Passive | Iontophoresis | Passive | Iontophoresis |
| Mean | 942 | 3818 | 1875 | 8260 |
| Standard deviation | 149 | 1255 | 530 | 2205 |

Amounts are expressed as mean ± SD ($ng/cm^2$).

For both CnIIIC and the CnIIIC variant of SEQ ID No8, iontophoresis enabled a significant increase in the amounts deposited as compared to passive delivery. When comparing the mean values of iontophoretic versus passive conditions, the highest effect—i.e. a 12-fold increase in the amount deposited was observed with CnIIIC variant of SEQ ID No8 at a concentration of 0.1 mM after 5 minutes at 0.5 $mA/cm^2$.

To a first approximation, passive diffusion of the CnIIIC variants at 0.1 mM for 8 hours resulted in similar skin deposition to iontophoresis of the same formulations at a current density of 0.5 $mA/cm^2$ for 15 minutes, although the values after current application tended to be higher.

CnIIIC and CnIIIC Variants Biodistribution

The deposition experiments were of interest since they enabled comparison of the amounts of the different analogues present in the skin following formulation application with the different treatment conditions. However, it is significant interest to determine their biodistribution since this can reveal the amounts present in the different skin layers. Deposited amounts of CnIIIc and variants thereof were evaluated in the different layers of the skin after passive and iontophoretic conditions, -i.e. current density of 0.25 mA/cm2 for an initial concentration of 40 μM of CnIIIC and variants thereof and an experiment of 5 minutes.

Figure 4:
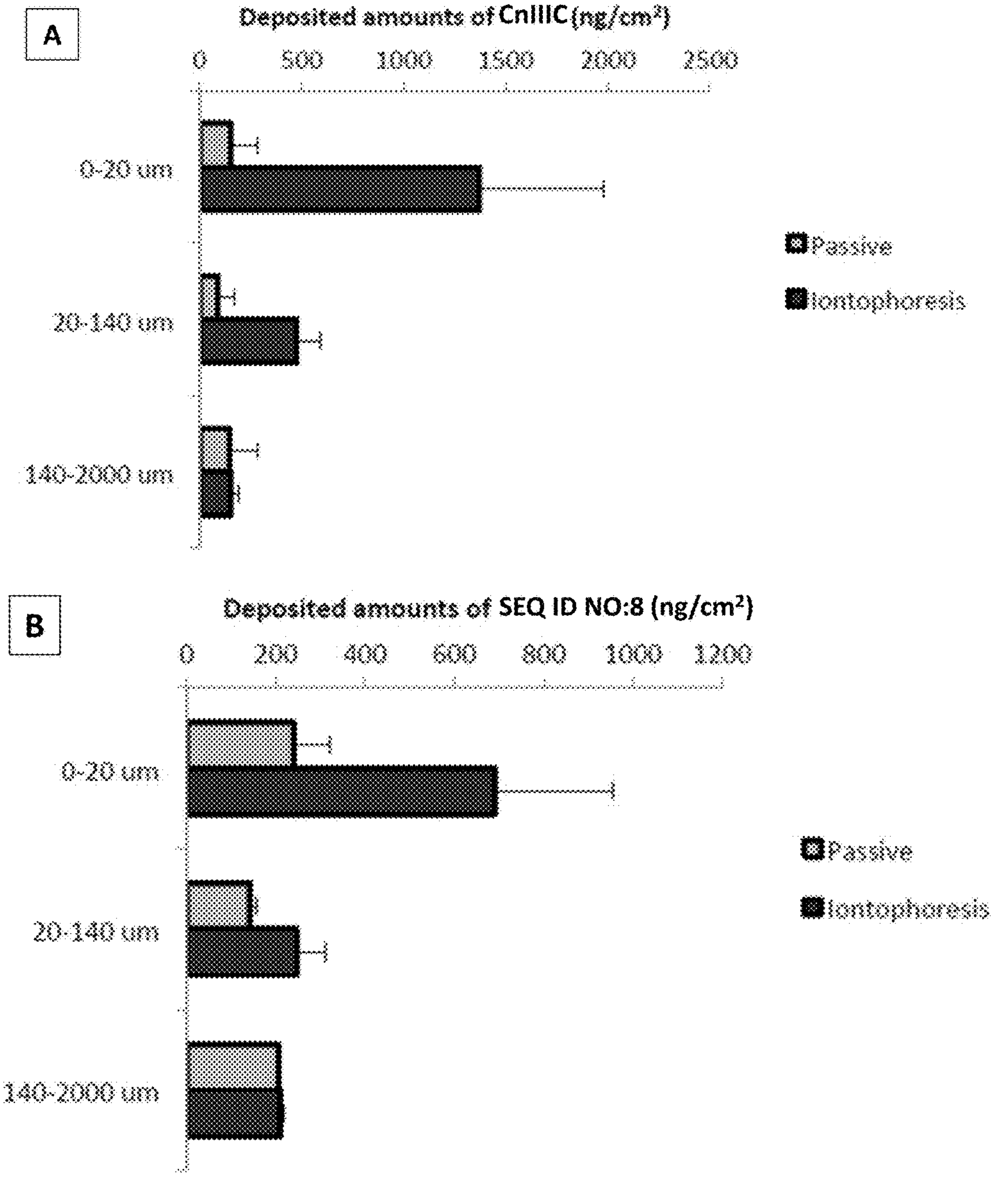
FIG. 4A shows deposited amounts of CnIIIC in the different layers of the skin after passive and iontophoretic conditions.
FIG. 4B shows deposited amounts of CnIIIC variant of SEQ ID N°8 in the different layers of the skin after passive and iontophoretic conditions.

FIG. 4 shows deposited amounts of CnIIIC and CnIIIC variant of SEQ ID N°8 in the different layers of the skin after passive and iontophoretic conditions.

As illustrated in FIG. 4, for CnIIIC (FIG. 4-A) and CnIIIC variant of SEQ ID N°8 (FIG. 4-B), iontophoretic delivery of peptide resulted in major peptide deposition in the upper layer of skin -i.e. in the *stratum corneum.*

Example 9

In Vivo Clinical Evaluation of CnIIIC and Variants Thereof as Anti-Wrinkle Agent The objective of this study is to evaluate and to compare the in vivo anti-aging efficacy of CnIIIC and variants thereof.

11 healthy Caucasian women aged between 57 and 65 years old displaying wrinkles and/or fine lines on the crow's feet with a grade 2 to 5 (according to a modified Bazin's scale) and under the eyes with a grade from 2 to 5 (according to the Bazin's scale) were recruited. The application of the test products is carried out by the subjects themselves at home, at a frequency of application of 2 times/days (morning and evening) for 14 days. A placebo is applied on one randomized half-face and the CnIIIC (2.5 μM) or variants thereof is applied on the other randomized half-face. The selection of the products to be applied on each half face (right and left) is determined at random for each subject using a specific software designed for this purpose.

This study is carried out as a "double blind study". Neither the participating subjects nor the Investigator are aware of the type of products being tested throughout the study; only the Study Sponsor is aware of the nature of the test products.

This study is a comparative study where the results obtained after application of one of the test products to one test area are compared with the results obtained after application of the other test product to the other test area The subjects do not serve as their own reference.

The subjects serve as their own reference and the results obtained at various assessment times are compared with those obtained at T0.

The Evaluation is Performed Using:

- in vivo clinical evaluation by one expert (crow's feet and under eyes wrinkles): the expert assesses in vivo the main wrinkle depth on the crow's foot of a subject from a structured scale in 9 points developed from a modified Bazin's scale. This scale is from 0 (no depth (because of the absence of wrinkle) to 8 (very deep wrinkle). The expert assesses in vivo the main wrinkle depth on the under eyes area of a subject according to the scale of the book "Atlas du vieillissement cutané—Vol1. Population Européenne—R. Bazin et E. Doublet" in 6 points. This scale is from 0 (no depth, absence of wrinkle) to 5 (very deep wrinkle). The evaluation is carried out in a room under monitored temperature and relative humidity (temperature: 21±1° C., hygrometry: 45±5%). A 20-minute period of acclimatisation in the air-conditioned room is respected for the subject prior the measurements (temperature: 21±1° C., hygrometry: 45±5%). She wears a paper cap. The subject is sitting on a chair behind an evaluation table composed of 3 neon lights and created by Spincontrol to carry out the clinical evaluations. The expert is sitting on a chair in front of the subject, on the other side of the evaluation table. For the evaluation of the wrinkles on the crow's foot, the subject turns the head on ¾ during the evaluation of each crow's foot and looks at a mark on the wall to have the good position. The position of the subject is reproducible by locating the position of the chair and of the evaluation table. The evaluation is carried out on both crow's feet and both under eyes area wrinkles. The beautician carries out the evaluation of the depth of the subject's wrinkle using the dedicated scale. The expert records the evaluated grade on the subject's case report form. The notation in 0.4 and 0.6 is allowed. This technique is considered as operator-dependent: for a given subject, the measurements are performed by the same technician at all the kinetics time points. The result is given in term of a grade from 0 to 8 for the crow's feet wrinkles and from 0 to 5 for the under eyes wrinkles according to the dedicated scale. An overall smoothing of the wrinkles is shown by a decrease in grade of wrinkles.,
- in vivo fringe projection by AEVA-HE System on the crow's feet and under eyes wrinkles: Based on the technique of fringe projection combined with stereometry, the AEVA-HE (Eotech) system offers high resolution 3D digitization, enabling to evaluate the relief modifications (examples: nasogenian groove, wrinkles, fine lines . . .) and the volume modifications of the face (examples: jaw lines, eye bags . . . ). The measurements are performed by using a fringe projection system (halogen projector 2203) coupled with 2 high resolution cameras (AVT Pike F-505B and AVT Pike F-505C), equipped with 3 objectives of field 250 mm (Breuckman, Germany—Eotech, France) and associated with the acquisition software OPTOCAT 2010R2 (Breuckman, Germany—Eotech, France). The AEVA-HE system is installed on the Motorised Visio-4D bench enabling the positioning and the repositioning of the subjects at various measurement time points and making reliable before/after comparisons. The lighting system coupled with 2 video cameras in stereometry enables the projection of sequences of lattice lines onto the object (fringes). The three-dimensional information about the object is calculated from the deformations of these fringes on the object's surface and recorded by the 2 digital cameras. The measures are carried out in a dark room. The subject must wear a mobcap on the head, keep the eyes open and look in a mirror attached to the structure of the Visio-4D in order to control the inclination of their head. The positioning of the sensor and of the subject is made easier with the use of the measurement bench (Visio-4D) which enables the face to be kept in the same position and a reproducible positioning of the sensor beside the studied area. Two acquisitions are carried out, on the right and the left half face. These two acquisitions are realigned and recorded in one file. This technique is not considered as operator-dependent: for a given subject, the measurements can be performed by different technicians at the various kinetics time points. The analysis of the cutaneous topography of the surface is carried out by calculating the parameters of standard roughness. These parameters are extracted from a surface of 124×103 mm (128 cm2). The analysis of the data obtained by fringe projection on the studied areas is carried out using both the TopoSurf and Optocat analysis systems. The analysis is performed on the "SDF" files obtained from the "ABS" files. The principle involves quantifying the micro-relief of the studied area by analysing the deformation of high contrast networks of lines on this surface. The parameters are quantified on a serial of profiles perpendicular to the wrinkles and fine lines on the area of interest.

SR: Developed Surface. (Arbitrary units)

SQ: Roughness with regard to the average quadratic variation.(mm). Average variations in amplitude of the relief integrated into the studied surface. A decrease in this parameter means a smoothing of the surface and a decrease in the wrinkles and fine lines.

ST: maximum amplitude of the relief. (mm). The decrease in ST means a reduction of the main wrinkle. This parameter is sensitive to artefacts.

SA: Average roughness (mm). Average variations in amplitude of the relief integrated into the studied surface. A decrease in this parameter means a smoothing of the surface and a decrease in the wrinkles and fine lines.

Stm: Mean difference between peeks and valleys. (mm). A decrease means a smoothing of the studied surface.

Wrinkles and fine wrinkles are detected after the use of several filters and a polynomial correction for removing the local shape and flattened the area of interest. Area of the main wrinkle ($mm^2$): this parameter corresponds to the area of detected main wrinkle in the area of interest. Volume of the main wrinkle (mm3):

this parameter corresponds to the volume of detected main wrinkle in the area of interest. At the end of the study, the reconstituted "T0—T+14 days" iconographies of 2 cases (average and best) will be provided to the study sponsor., illustrative photographs of the crow's feet and under eyes wrinkles: this technique consists of obtaining high resolution photographs of the area at the corner of the eye corresponding to the wrinkles of the "crow's feet and the area under the eye", for an illustrative aim, in diffuse light, in completely reproducible lighting conditions. The acquisitions are carried out with a high resolution camera with a 60 mm lens. The diffuse light source is ensured by one flash equipped with a diffusion screen. Images are taken in the TIFF RGB file format to ensure a good storage of raw colour without any processing. The acquisitions are conducted in a room under monitored temperature and relative humidity (Temperature: 21±1° C., hygrometry: 45±5%). 20 minute period of acclimatization in the air-conditioned room is respected. The subject wears a black paper cap and a black cloth in order to avoid the potential influence of extrinsic colours. The subject has opened eyes during the acquisitions. To ensure a good reproducibility of the acquisition conditions, the photographs of the crow's foot are carried out on an optical measurement bench especially developed by Spincontrol (Visio-Face®). This bench allows us to keep the face in the same position and the photographic acquisition system in perfectly defined positions. The studied areas are the right and the left crow's feet and under eyes areas. One photograph is taken on the studied area only on 4 subjects among the entire selected panel. At Tn, the visualisation of the initial digital photograph (T0) ensures a good repositioning of the subject. This technique is not considered as operator-dependent: for a given subject, the photographs acquisition can be performed by different technicians at the various kinetics time points., and self assessment questionnaire: the subjects have to fill in a questionnaire in order to evaluate their overall opinion and their attitude towards the effectiveness of the product(s) being tested.

For each item, the possible answers are:

"Completely agree",

"Somewhat agree",

"Somewhat disagree",

"Completely disagree".

The subjects are in front of a mirror with a standardized light and fill in the questionnaire individually without any extrinsic influences (other volunteers, results of technical measurements). The filling-out of the questionnaire is performed under control of a technician who checks the acquisition according to an operating method. The subjects complete one questionnaire per treated half face. This technique is not considered as operator-dependent: for a given subject, the questionnaires collection can be performed by different technicians at the various kinetics time points. The questionnaires are carried on and exploited with dedicated software reachable from an Internet browser. The raw data are treated and analyzed with Excel (Microsoft).

For Both Data Analysis and Technical Data, the Results Include:

Raw values for each subject at each measurement time.

Deviations from T0 for each subject at each measurement time (Tn-T0)

Means, medians, maximum, minimum and standard deviations of the raw values and of the differences with respect to TO obtained for the entire panel.

Variations, with regards to T0 expressed as a percentage calculated from the mean values only for the fringe projection measurements.

The number and the percentage of subjects presenting an improvement. Considering the number of the subjects (11), no statistical data treatment is carried out.

The analysis of data obtained from the self-evaluation questionnaires involves the creation of the frequency tables that take into account the number of responses and calculate the frequency of the different possible answers (expressed in percentages) to each qualitative question. For each question, results are presented in tables (number of answers and frequencies). To evaluate the efficacy and the appreciation of the product(s), for each item, two percentages Z1 and Z2 are calculated, as follows:

Z1=Favorable opinion (i.e.: “Completely agree”+“Somewhat agree”)

Z2=Unfavorable opinion (i.e.: “Completely disagree”+ “Somewhat disagree”).

Considering the number of the subjects (11), no statistical data treatment is carried out.

Results for in Vivo Clinical Evaluation by One Expert:

The following table presents the means and the standard error of the mean of the evolutions of the wrinkles grades (Grade score: CFW-Gr CdT, % of reduction CFW-Gr CdT%) attributed by the expert on the crow’s foot by the CnIIIC.

| | CFW-Gr C0 | CFW-Gr C14 | CFW-Gr CdT | CFW-Gr CdT % |
|---|---|---|---|---|
| Mean | 4.291 | 4.055 | −0.236 | −5.231 |
| SEM | 0.228 | 0.200 | 0.080 | 1.670 |
| SD | 0.756 | 0.664 | 0.266 | 5.537 |
| Median | 4.400 | 4.400 | −0.200 | −5.556 |
| Min | 3.400 | 3.000 | −0.800 | −14.815 |
| Max | 5.400 | 5.000 | — | — |

Figure 5:
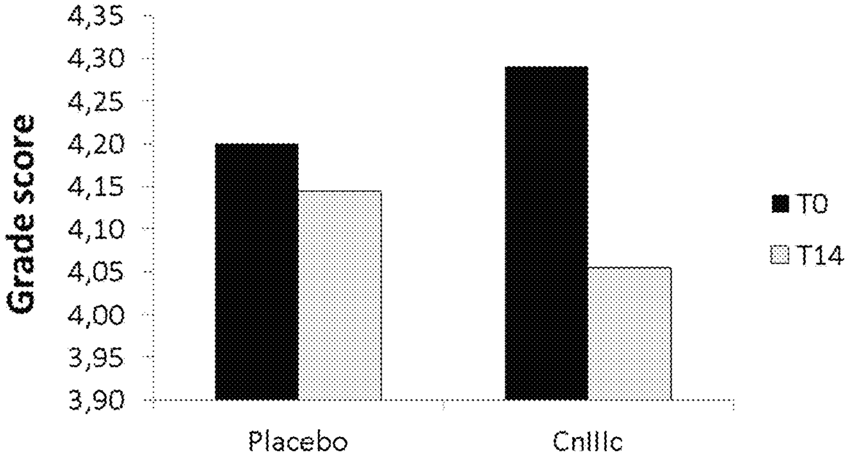
FIG. 5 shows the effects of CnIIIC on Crow's feet wrinkles grade score.

After 14 days of application of the product containing CnIIIC (2.5 μM), the main crow’s foot wrinkle decreased of −0.236 (−5.231%) grade out of 8 on average on the whole panel, compared to placebo with −0.055 (−1.53%). Results are illustrated in FIG. 5 which shows the grade score for both placebo and CnIIIC containing products.

6 subjects out of 11 (i.e. 55% of the panel) show an improvement in the crow’s foot wrinkles grade at T+14 days;

Results for in vivo fringe projection on the crow’s feet (AEVA-HE System):

The Studied Profile Parameters Are:

ST: maximum amplitude of the relief. (mm)

SA: Average roughness (mm)

SQ: Roughness with regard to the average quadratic variation.(mm)

SR: Developed Surface. (Arbitrary units)

Stm: Mean difference between peeks and valleys. (mm)

The Studied Morphology Parameters Are:

Volume of the main wrinkle (mm3), and

Area of the main wrinkle ($mm^2$).

The following table presents the means, % reduction (CFW-CdT %), the standard error of the mean of the evolutions (Tn-T0) of the volume (CFW-Vo) and area (CFW-Ar) of the main wrinkle observed on the crow’s foot wrinkles treated by CnIIIC.

| | CFW-Vo C0 | CFW-Vo C14 | CFW-Vo CdT | CFW-Vo CdT % | CFW-Ar C0 | CFW-Ar C14 | CFW-Ar CdT | CFW-Ar CdT % |
|---|---|---|---|---|---|---|---|---|
| Mean | 1.019 | 0.823 | −0.195 | −13.847 | 10.132 | 8.909 | −1.224 | −12.178 |
| SEM | 0.197 | 0.151 | 0.117 | 14.993 | 1.205 | 1.205 | 0.810 | 8.557 |
| SD | 0.624 | 0.477 | 0.370 | 47.413 | 3.811 | 3.809 | 2.560 | 27.058 |
| Median | 0.949 | 0.871 | −0.198 | −29.049 | 10.484 | 8.725 | −2.109 | −20.910 |
| Min | 0.239 | 0.104 | −0.771 | −56.485 | 4.561 | 2.476 | −4.276 | −45.714 |
| Max | 2.319 | 1.798 | 0.478 | 98.760 | 16.954 | 14.464 | 3.357 | 39.440 |

Both the volume and area of the main wrinkle observed on the crow’s feet are reduced when treated CnIIIC.

The following tables present the means, % reduction (CFW-CdT%), the standard error of the mean of the evolutions (Tn-TO) of the rugosity parameters ST (CFW-ST), SA (CFW-SA), SQ (CFW-SQ), SR (CFW-SR) and Stm (CFW-Sm) observed on the crow’s foot wrinkles treated by CnIIIC.

| | CFW-ST C0 | CFW-ST C14 | CFW-ST CdT | CFW-ST CdT % | CFW-SA C0 | CFW-SA C14 | CFW-SA CdT | CFW-SA CdT % |
|---|---|---|---|---|---|---|---|---|
| Mean | 0.637 | 0.600 | −0.038 | −5.602 | 0.046 | 0.044 | −0.002 | −4.725 |
| SEM | 0.030 | 0.036 | 0.027 | 4.593 | 0.003 | 0.003 | 0.002 | 3.589 |
| SD | 0.094 | 0.115 | 0.086 | 14.525 | 0.011 | 0.010 | 0.005 | 11.350 |
| Median | 0.625 | 0.619 | −0.040 | −6.612 | 0.042 | 0.041 | −0.003 | −6.306 |
| Min | 0.519 | 0.416 | −0.191 | −31.454 | 0.037 | 0.029 | −0.008 | −21.951 |
| Max | 0.781 | 0.796 | 0.114 | 21.284 | 0.068 | 0.063 | 0.007 | 16.129 |

| | CFW-SQ C0 | CFW-SQ C14 | CFW-SQ CdT | CFW-SQ CdT % | CFW-SR C0 | CFW-SR C14 | CFW-SR CdT | CFW-SR CdT % |
|---|---|---|---|---|---|---|---|---|
| Mean | 0.063 | 0.059 | −0.004 | −5.709 | 1.043 | 1.039 | −0.004 | −0.405 |
| SEM | 0.005 | 0.004 | 0.002 | 3.611 | 0.006 | 0.007 | 0.003 | 0.329 |
| SD | 0.014 | 0.014 | 0.007 | 11.418 | 0.019 | 0.023 | 0.011 | 1.039 |
| Median | 0.057 | 0.056 | −0.005 | −7.108 | 1.042 | 1.033 | −0.000 | −0.005 |
| Min | 0.048 | 0.037 | −0.013 | −23.333 | 1.011 | 1.011 | −0.020 | −1.918 |
| Max | 0.092 | 0.084 | 0.009 | 14.783 | 1.084 | 1.099 | 0.015 | 1.394 |

| | CFW-Sm C0 | CFW-Sm C14 | CFW-Sm CdT | CFWSm CdT % |
|---|---|---|---|---|
| Mean | 0.339 | 0.321 | −0.018 | −5.287 |
| SEM | 0.012 | 0.018 | 0.013 | 3.825 |
| SD | 0.038 | 0.057 | 0.041 | 12.096 |
| Median | 0.334 | 0.309 | −0.008 | −2.638 |
| Min | 0.292 | 0.229 | −0.091 | −28.406 |
| Max | 0.410 | 0.416 | 0.047 | 12.581 |

Figure 6:
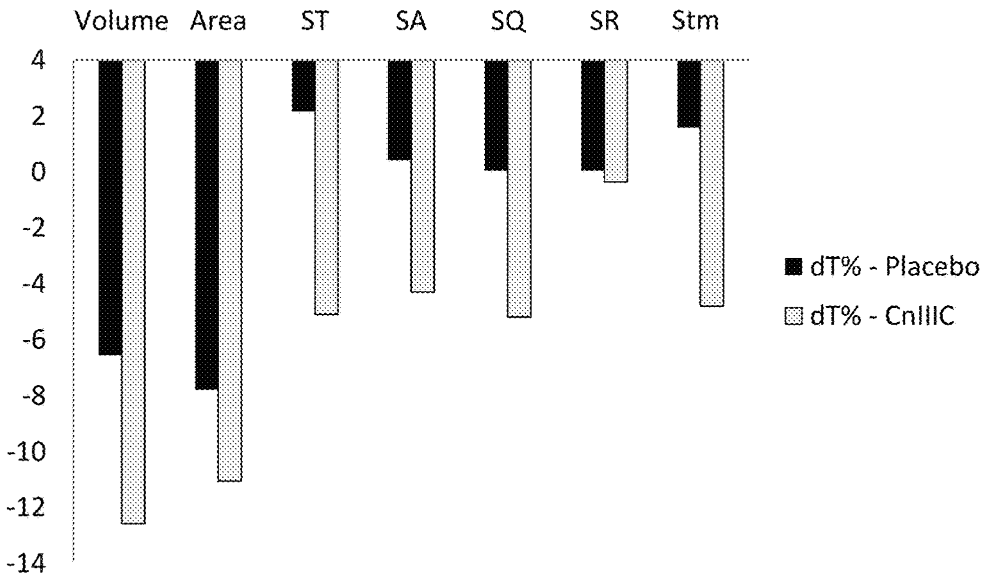
FIG. 6 shows the effects of CnIIIC on Crow's feet wrinkles morphology and rugosity.

The results obtained for CnIIIC (dT %-C) compared to placebo (dT %-A) on morphology (Area and Volume) and rugosity parameters (ST, SA, SQ, SR and Stm) are illustrated in FIG. 6.

On the crow's foot, after 14 days of application of the product CnIIIC, the results show:

- Decreases in all the profile parameters, especially in the ST parameter, corresponding to the main wrinkle depth and SA parameter, corresponding to the average roughness of the analyzed area: −5.6% and −4.7% respectively, on average on the whole panel.
- Decreases in the volume and the area of the main wrinkle: −13.85% and −12.18% respectively, on average on the whole panel.

For the product CnIIIC, the results trend to show an improvement only the crow's foot, through the decrease in the profile and morphology parameters. The decrease in the ST parameter (−5.6%) and in the SA parameter (−4.7%) trend to show respectively a reduction in the main wrinkle depth and an improvement in the average roughness of the crow's foot area; whereas the decrease in the morphology parameters trend to show a decrease in the main wrinkle volume (−13.85%) and area (−12.18%) of the crow's foot.

Results on the Self-Assessment Questionnaires:

After 14 days of application, in terms of cosmetic appreciations, 64% of the subjects recognize that both products penetrate quickly. The product CnIIIC seems to be more appreciated for its "pleasant texture" with 64% of agreement against 45% for the placebo.

After 14 days of application, in terms of efficacy, both products receive equal judgment for being "quickly effective" (55% of agreement) as well as for their positive effect on skin hydration (64% of positive agreement), skin softness (82%) and skin smoothness (73%). The subjects seem to give a better appreciation to the product CnIIIC, for leaving the skin "firmer" and "lifted" with 55% of agreement in each case, against 45% for the placebo.

The same clinical study was performed using a CnIIIc variant (SEQ ID NO:8).

A second clinical study was implemented for CnIIIC variants versus placebo, versus "Botox-like" benchmark (Argireline) and versus wrinkle benchmark (Retinol or vitamin C). A total of 210 panelists is recruited for this study.

A twice daily application on full face is used for 56 days. Each group of panelist contains 30 subjects. Short and long terms effects are evaluated at time points 0, 2 h, 5 h, 14 days, 1 month and 2 months. Crow's feet, eye contour and lion wrinkles (deep wrinkle) are treated area.

The Evaluation is Performed Using:

- in vivo clinical evaluation by one expert,
- in vivo fringe projection by AEVA-HE System on the crow's feet, under eyes and lion wrinkles,
- illustrative photographs of the crow's feet, under eyes and lion wrinkles, and,
- self assessment questionnaire.

The invention claimed is:

1. A cosmetic process for treating wrinkles and fine lines, comprising topically applying to the skin a composition comprising as an active substance, and in an amount ranging from 0.05 x $10^{-6}$ to 1 x $10^{-3}$ percent by weight of the total weight of the composition, a variant of a mu-conotoxin peptide comprising an amino acid sequence having at least 92% identity to SEQ ID NO: 2, wherein said variant is engineered to have one substituted amino acid at an amino acid position selected from the group consisting of 1, 5, 8, 11, 13, 14, 18 and 19 of SEQ ID NO: 2.

2. The cosmetic process of claim 1, wherein the variant of the mu-conotoxin peptide further comprises an N-terminal modification at the N-terminal amino acid position.

3. The cosmetic process of claim 1, wherein the variant of the mu-conotoxin peptide is selected from the group consisting of: SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

4. The cosmetic process of claim 1, wherein the N-terminal amino acid of said variant is a Lysine (K) residue.

5. The cosmetic process of claim 2, wherein the N-modification is selected from the group consisting of myristoylation, decanoylation, laurylation, stearylation, oleylation and palmitoylation.

6. The cosmetic process of claim 4, wherein the N-terminal amino acid of said variant is a Lysine (K) residue and the N-modification is selected from the group consisting of myristoylation, decanoylation, laurylation, stearylation, oleylation and palmitoylation.

7. The cosmetic process of claim 1, wherein an anti-wrinkle and fine lines effect is observed for 20 minutes to 48 hours, or longer from the topical application of the composition to the skin.

8. The cosmetic process of claim 1, wherein a 5% reduction in wrinkles and fine lines appearance is visible after 2 hours of topical application of the composition to the skin.

9. The cosmetic process of claim 1, wherein the composition is administered with a device to enhance the permeation.

10. The cosmetic process of claim 9, wherein the device is an iontophoresis device.

11. The cosmetic process of claim 1, wherein the variant comprises a substitution selected from the group consisting of Z1K, N5D, N5E, N5Q, K8R, S11T, K13R, W14F, W14Y, H18R, and A19S.

* * * * *